United States Patent [19]

Pennino et al.

[11] Patent Number: 5,261,906
[45] Date of Patent: Nov. 16, 1993

[54] ELECTRO-SURGICAL DISSECTING AND CAUTERIZING INSTRUMENT

[76] Inventors: Ralph Pennino, 255 S. Danbury Cir., Rochester, N.Y. 14168; Timothy O'Connor, 160 Whitewood La., Rochester, N.Y. 14618; Robert D. Rambo, 702 Simmons Rd., Sellersville, Pa. 18960

[21] Appl. No.: 804,052

[22] Filed: Dec. 9, 1991

[51] Int. Cl.$^5$ ............................................. A61B 17/39
[52] U.S. Cl. ............................................. 606/46; 606/41; 606/45; 606/49
[58] Field of Search ............................ 606/43–52, 606/32, 41

[56] References Cited

U.S. PATENT DOCUMENTS

| 373,399 | 11/1887 | Hamilton | 606/51 |
|---|---|---|---|
| 1,930,214 | 3/1931 | Wappler. | |
| 2,417,530 | 3/1947 | Weiser | 606/43 |
| 3,707,149 | 12/1972 | Hao et al. | 606/49 X |
| 4,311,143 | 1/1982 | Komiya | 606/47 |
| 4,517,975 | 5/1985 | Garito. | |
| 4,593,691 | 6/1986 | Lindstrom et al. | 606/49 X |
| 4,887,593 | 12/1989 | Wiley | 606/45 |
| 4,919,129 | 4/1990 | Weber, Jr. et al. | 606/45 X |
| 4,924,882 | 5/1990 | Donovan | 128/898 |
| 4,985,035 | 1/1991 | Torre | 606/167 |
| 5,019,076 | 5/1991 | Yamanashi et al. | 606/49 |
| 5,080,660 | 1/1992 | Buelna | 606/45 |

FOREIGN PATENT DOCUMENTS

| 0308690 | 3/1989 | European Pat. Off. | 606/32 |
|---|---|---|---|
| 2639157 | 3/1978 | Fed. Rep. of Germany | 606/41 |

Primary Examiner—Stephen C. Pellegrino
Assistant Examiner—Jeffrey A. Schmidt
Attorney, Agent, or Firm—Katherine McGuire

[57] ABSTRACT

An electro-surgical dissecting and cauterization tool comprises a linear, rigid insulating sleeve surrounding means providing an electric conducting path between a proximal, electric plug end and working tip electrode distal end. The plug attaches the tool to a conventional electro-surgical unit which supplies electrical energy to the working tip electrode end of the tool. A rigid arm extends between the sleeve and the working tip electrode and includes portions laterally offset from the main axis of the sleeve to increase visualization of the working tip electrode during surgery.

5 Claims, 2 Drawing Sheets

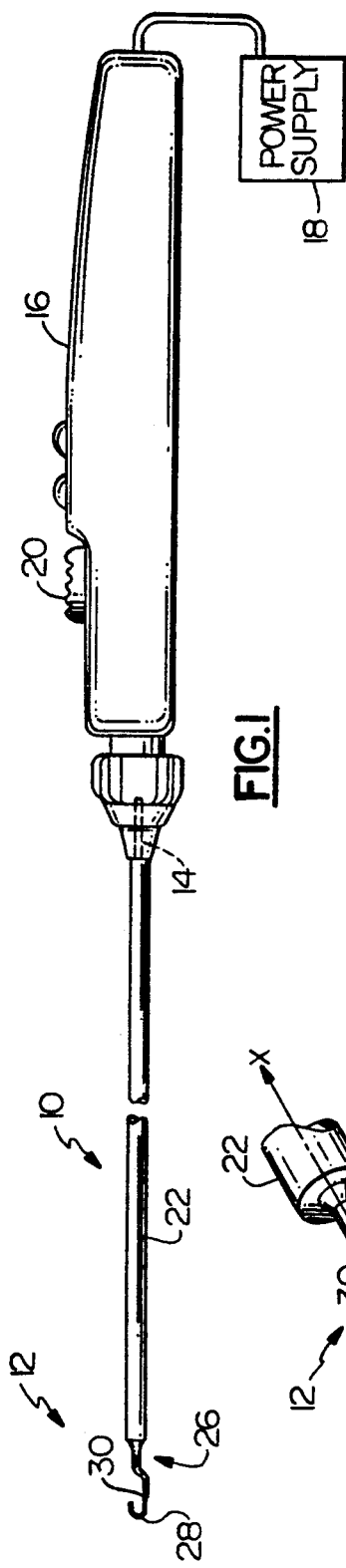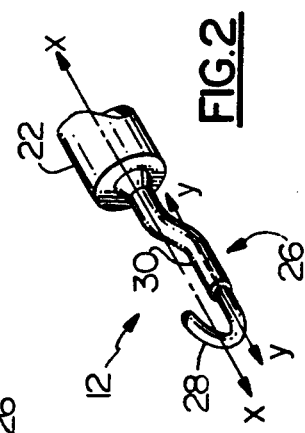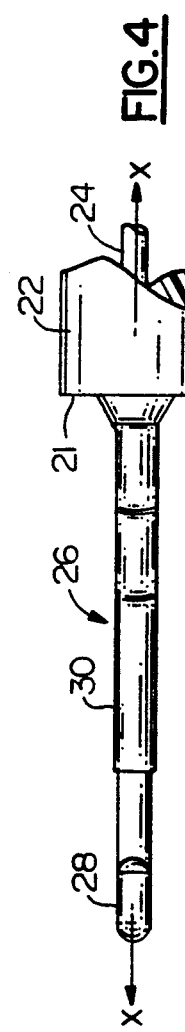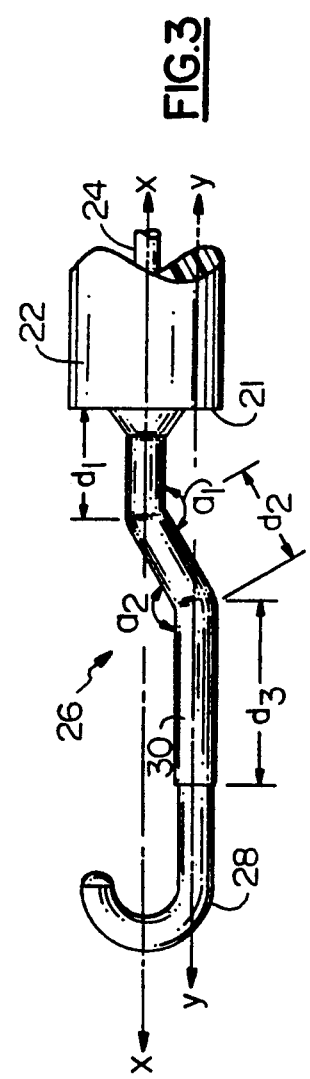

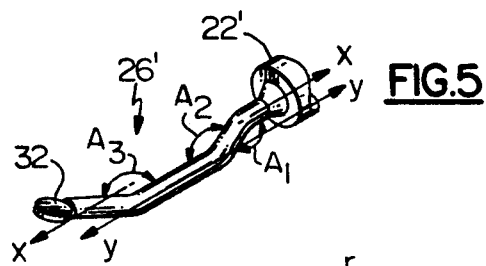
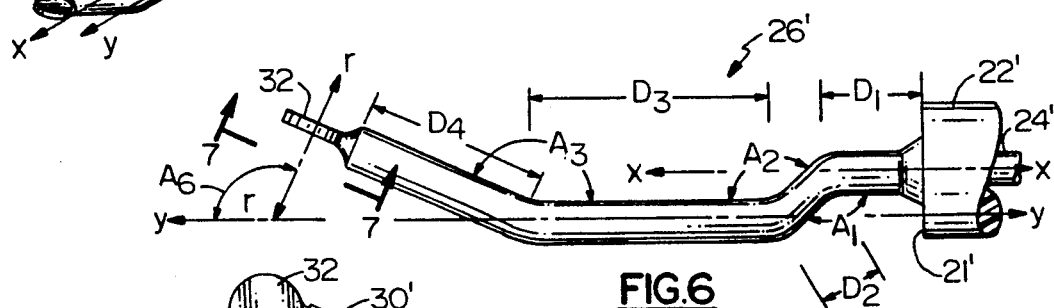
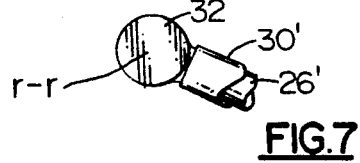
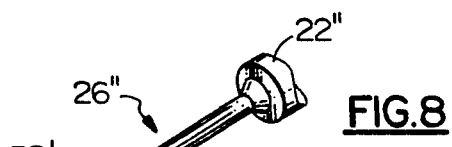
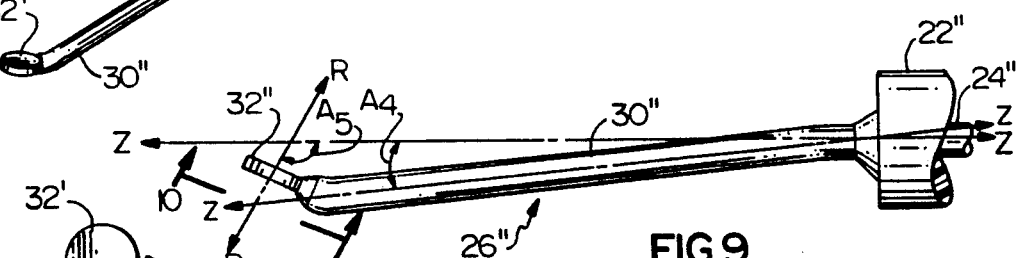
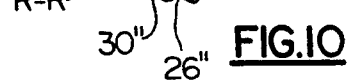

5,261,906

ELECTRO-SURGICAL DISSECTING AND CAUTERIZING INSTRUMENT

BACKGROUND OF THE INVENTION

This invention relates to surgical instruments and, more particularly, to a novel electro-surgical dissection and cauterization instrument for use primarily in laparoscopic/endoscopic procedures.

Many surgical procedures of today involving the removal and/or cauterization of tissue (e.g. endometriosis, lysis of adhesions, cholecystectomy, appendectomy, etc.) are performed with an electro-surgical dissection and cauterization instrument either in open surgery where the surgeon has direct view and access to the operation site, or in combination with an endoscope. Referring to the endoscopic surgery and, in particular, laparoscopic surgery which refers specifically to the abdominal area, the surgeon first makes usually several small, spaced incisions through the abdominal wall of the anesthetized patient. A source of compressed $CO_2$ is then delivered through one of the incisions to inflate the abdomen which effectively raises the abdominal wall above the organs and intestines of the patient. A space is thereby created therebetween which facilitates manipulation of surgical instruments which have been inserted into the abdomen through one of the incisions.

The surgeon views the internal operation site with a laparoscope which is a specialized type of scope inserted into the abdomen through an incision. The laparoscope is attached to a miniaturized, surgical camera assembly which operates by transmitting the image the camera is directed at inside the abdomen of the patient to the laparoscope eyepiece and/or a CRT screen in the operating room. A trochar is typically positioned within the incision to provide a smooth passageway for the instruments into and out of the abdomen. The electro-surgical instrument passes through the trochar to reach and perform surgery on the patient by the surgeon carefully manipulating the exposed end of the instrument.

Electro-surgical instruments are used primarily to separate and remove diseased tissue from healthy tissue such as polyps from the colon, for example. They are also used as probes to move tissue about during exploratory surgery. Supplying the instrument with controlled, electrical energy is well known in the art. With the patient properly grounded, a high frequency electric current is discharged at the distal, electrode end of the tool which augments its cutting capability while simultaneously cauterizing bleeding tissue and blood vessels. The electro-surgical instrument includes a proximal end with a plug permitting connection of the tool to an electro-surgical unit which supplies electric energy to the distal, electrode end of the tool. A rigid, linear insulating sleeve surrounds the instrument which delivers electric energy from the proximal, plug end to the distal, electrode end which itself is formed of electrically conductive material such as stainless steel.

The instrument's distal electrode may be found in a variety of configurations, each different configuration serving a different, specific function. For example, a working tip electrode in the shape of a snare or hook is used for grasping and pulling at tissue while a working tip electrode in the shape of a flattened spatula is used primarily to move tissue about and/or to cauterize bleeding tissue. Many other working tip electrode configurations appear on the market every day as the needs and likes of surgeons change.

In most, if not all, of the dissecting tools available today, the working tip electrode of the instrument just described extends directly from the distal end of the insulating sleeve. As such, there is a minimum of distance between the sleeve and the working tip electrode which, in many instances of use, obstructs or impairs the surgeon's view of the operation site as viewed in either complete open surgery or with a laparoscope during the procedure just described. The problem exists due to the small size of the working tip electrode in relation to the relatively large diameter of the sleeve from which it extends.

A second problem surgeons have reported when using present day electro-surgical instruments is that the portion of the working tip electrode directly adjacent the sleeve occasionally makes inadvertent contact with healthy tissue surrounding the surgical work site. This has resulted in unintentional cauterization of healthy tissue which poses serious consequences to both patient and surgeon alike.

It is therefore a principle object of the present invention to provide an electro-surgical instrument including a rigid arm extending between the distal, working tip electrode and the insulating sleeve. The arm includes at least a portion thereof laterally offset from the longitudinal axis of the sleeve whereby obstruction of the surgeon's view of the working tip electrode and surgical work site by the sleeve is substantially reduced.

It is a further object of the present invention to provide an electro-surgical instrument which provides an electrical insulating layer along the entire length of the tool up to the exposed working tip electrode such that inadvertent cauterization of tissue with portions of the tool other than the working tip electrode is eliminated.

It is another object of the present invention to provide a single-use, disposable, electro-surgical and cauterizing instrument for endoscopic procedures which is designed for easy handling and use by the surgeon.

Other objects will in part be obvious and in part appear hereinafter.

SUMMARY OF THE INVENTION

In accordance with the foregoing objects, the invention comprises an electro-surgical dissecting and cauterizing instrument for use primarily in standard endoscopic procedures which include the use of an endoscope to view the operation. The instrument has also proved very useful in open surgeries which do not include the use of an endoscope. An electric plug is included at the instrument's proximal end for connecting the tool to a conventional, electro-surgical unit which supplies high frequency electric energy to the working tip electrode of the tool at the control of the surgeon. The electric energy is delivered to the distal, working tip of the tool via a conductive rod surrounded by a linear, rigid sleeve formed of an insulating material, the sleeve extending from the plug end to the distal end of the tool which includes the working tip electrode.

The distal end of the tool includes an electrically conductive, rigid arm extending from the sleeve portion of the tool. Although several embodiments of the tool will be described in detail below, in each embodiment of the tool the arm extends from the sleeve and includes portions laterally offset from the longitudinal axis of the sleeve. The working tip electrode is formed at the free end of the arm and is used to make direct contact with the patient at the internal operation site. A thin jacket of insulating material is disposed upon the arm from the point where it extends from the sleeve right up to, but not including, the working tip electrode.

The working tip electrode comes in many different shapes depending on the needs of the surgeon in a particular surgical application. Electrode tips to be described in detail below include a hook and flattened spatula, for example. The fact that portions of the arm which extend between the sleeve and working tip are laterally offset from the main axis of the sleeve provides for maximum visualization of the working tip electrode and operation site by the surgeon.

BRIEF DESCRIPTION OF THE DRAWINGS

FIG. 1 is a side, elevational view of a first embodiment of the electro-surgical dissecting and cauterizing instrument shown operably connected to a conventional, electro-surgical unit in the intended manner;

FIG. 2 is a perspective, fragmentary view of the distal working tip end of the electro-surgical instrument seen in FIG. 1;

FIG. 3 is a side, elevational, enlarged view of the distal end of the electro-surgical instrument seen in FIG. 2;

FIG. 4 is a top view of FIG. 3;

FIG. 5 is a perspective, fragmentary view of a second embodiment of the distal end of the electro-surgical instrument;

FIG. 6 is an enlarged, side, elevational view of FIG. 5;

FIG. 7 is a bottom, fragmentary view of the working tip end of the arm as taken along the line 7—7 in FIG. 6;

FIG. 8 is a perspective, fragmentary view of the distal end of a third embodiment of the electro-surgical instrument;

FIG. 9 is an enlarged, side, elevational view of FIG. 8; and

FIG. 10 is a bottom, fragmentary view of the working tip end of the arm as seen along the line 10—10 in FIG. 9.

DETAILED DESCRIPTION

Referring now to the drawings, there is seen in FIG. 1 a first embodiment of the electro-surgical dissecting and cauterizing instrument 10 including a distal, working end 12 and a proximal end 14 which includes an electric plug such that instrument 10 may be releasably and operably connected to a conventional, electro-surgical control unit 16. Control unit 16 is supplied high frequency, electrical energy via power supply 18 and further includes a switch means 20 which is used to control the flow of electrical energy from unit 16 to instrument 10. As such, a surgeon manually grasps unit 16 to work instrument 10 as described below. Although unit 16 is shown and described herein for the purpose of illustrating a typical electrical unit with which instrument 10 would be used, it is understood that plug 14 may be easily adapted to connect to a variety of electro-surgical units available today.

Dissecting and cauterizing instrument 10 is used primarily in surgical procedures which may or may not include the use of an endoscope to view the operation site. For purposes of description, the surgical procedure using an endoscope will be discussed. Also, surgical procedures of the type discussed herein are termed laparoscopic because they target the abdominal area. The type of endoscope used in the abdomen is therefore termed a laparoscope. In particular, the surgeon inserts distal end 12 into the abdomen of the anesthetized patient through a trochar (not shown) positioned within an incision made in the abdominal wall. The operation site is viewed at the eyepiece of the laparoscope and/or on a CRT screen by passing the laparoscope (also not shown) through an adjacent incision in the abdomen which has been previously inflated with $CO_2$ as is customary surgical procedure in laparoscopic surgery of this type. The raising of the abdominal wall above the innards of the patient with the $CO_2$ creates a space therebetween which increases maneuverability of instrument 10 within the abdomen besides increasing the viewing area of the surgical site with the laparoscope. Examples of typical laparoscopic procedures in which dissecting and cauterizing instrument 10 would be used are lysis of adhesions, cholecystectomy and appendectomy.

Dissecting and cauterizing instrument 10 includes a rigid insulating sleeve 22 which surrounds conducting rod 24 extending from plug 14 to distal end 12. Distal end 12 is seen to include a rigid arm 26 extending from substantially the center of the distal end 21 of sleeve 22. A working tip 28 electrode in the shape of a hook in the embodiment of tool 10 seen in FIGS. 1-4 integrally extends from arm 26. Arm 26 and working tip electrode 28 are formed of electrically conductive material such as stainless steel and are supplied electrical energy via a conductive rod 24 extending through sleeve 22. A thin layer or jacket of insulating material 30 in the form of a TEFLON heat-shrink tubing is disposed upon arm 26 from sleeve 22 to the base of working tip electrode 28.

Prior art electro-surgical instruments of which the present inventors are aware do not include an arm such as 26 extending between the working tip electrode 28 and end of sleeve 22 but instead have their working tip electrodes extend directly from the sleeve. As such, the view of the operation site is obstructed because of the close proximity of the sleeve to the working tip electrode since the diameter of the sleeve is substantially larger than the size of the working tip electrodes. To overcome this problem, the present dissecting and cauterizing instrument 10 includes arm 26 to effectively space working tip electrode 28 from sleeve 22. Furthermore, arm 26 is seen to include portions laterally offset from the linear axis x—x extending through the center of sleeve 22 and arm 26. This feature also increases the visualization of the surgical work site by having the working tip electrode 28 extend from a portion of the arm 26 which lies along an axis y—y which is parallel to and spaced from linear axis x—x of sleeve 22.

Referring to FIG. 3, arm 26 is seen to extend linearly from sleeve 22 for a first length having a distance $d_1$ and bend downwardly at an approximately 150 degree angle $a_1$, with respect thereto for a second length having a distance $d_2$. Arm 26 then bends upwardly at an approximately 150 degree angle $a_2$ to extend for a third length having a distance $d_3$. As such, it may be seen that the first length of arm 26 labeled $d_1$ extends along linear axis x—x of sleeve 22 which is spaced from and extends parallel to third length $d_3$. Working tip electrode 28 is seen to integrally extend from the distal end of third length $d_3$ and bend toward axis x—x to form a hook which is used primarily for pulling at tissue.

The electricity which flows through arm 26 and electrode hook 28 at the control of the surgeon augments the cutting capability of hook 28 and cauterizes bleeding blood vessels. To prevent unintentional cauterization with portions of instrument 10 other than hook 28, an insulating jacket 30 is disposed upon the entire length of arm 26.

Referring to FIGS. 5 and 6, a second embodiment of instrument 10 is seen. In this second embodiment, arm 26' linearly extends from sleeve 22' for a first length having a distance $D_1$ as with the embodiment of FIGS. 1-4, bending downwardly and then upwardly at approximately 135 degree angles $A_1$ and $A_2$ for second and third lengths having distances of $D_2$ and $D_3$, respectively. As such, the third length of arm 26' spanning distance $D_3$ lies along an axis Y—Y which is parallel to and spaced downwardly from the linear axis X—X of sleeve 22' where the first length of arm 26' spanning distance $D_1$ lies.

Arm 26' includes a third bend in an upwardly direction at an approximately 159 degree angle $A_3$ and extends linearly therefrom for a fourth length having a distance $D_4$, crossing linear axis X—X such that the working tip electrode 32 lies on the side of axis X—X opposite to which axis Y—Y lies. It will be noticed in FIGS. 5-7 that working tip electrode 32 is in the shape of a flattened spatula which has a radial axis r—r which intersects linear axis Y—Y. Spatula 32 proves especially useful for cauterizing bleeding blood vessels rather than removing tissue from the patient's body. An insulating jacket 30' is disposed upon arm 26' from the distal end of sleeve 22' to the base of working tip electrode 32 to prevent any portion of arm 26' from unintentionally contacting and cauterizing healthy tissue surrounding the operation site.

Referring now to FIGS. 8, 9 and 10 which show yet a third embodiment of the invention, arm 26" is entirely linear and extends from sleeve 22" along an axis z—z which makes an approximately 6 degree acute angle $A_4$ with linear axis Z—Z of sleeve 22". Working tip electrode 32', which is also in the shape of a substantially circular, planar spatula, extends upwardly from arm 26" toward axis Z—Z. Working tip electrode 32' has a radial axis R—R which intersects linear axis Z—Z at an obtuse angle $A_5$. An insulating jacket 30" is disposed upon arm 26" from sleeve 22" to working tip electrode 32'.

Based on the foregoing description of three embodiments of the invention, it may be realized that the length and configuration of the arms 26, 26' and 26" permit each of the respective working tip electrodes 30, 32 and 32' to be significantly spaced from and laterally offset from the longitudinal axis of the sleeve. This permits an enhanced viewing area of the surgical work site and working tip electrode for the surgeon. While the invention has been shown and described with particular reference to preferred embodiments thereof, it will be appreciated to those skilled in the art that variations in working tip electrode configuration and specific lengths and angles of the arm portion of the tool may be made to fit a particular surgical need without departing from the full scope of the invention as is set forth in the claims which follow.

What is claimed is:

1. An electro-surgical dissecting and cauterizing instrument for connection to a source of manually controllable, electric current, said instrument comprising:
   a. electric conducting means having proximal and distal ends, said electric conducting means proximal end forming a plug removably connecting said instrument to said source of manually controllable electric current;
   b. a rigid insulating sleeve having first and second ends and a constant outer diameter and lying along a first linear axis, said sleeve concentrically surrounding and electrically insulating said electric conducting means with said electric conducting means plug extending exteriorly of said sleeve first end and said electric conducting means distal end lying adjacent said sleeve second end, said conducting means providing a path through which said electric current may travel;
   c. a rigid, electrically conductive arm having first and second ends and an outer diameter smaller than said sleeve outer diameter, said arm first end electrically connected to said conducting means distal end and co-axially extending therefrom along said first linear axis for a first length thereof, said arm having a second length integrally extending from said first length and lying along a second linear axis which extends at an obtuse angle ($a_1$) to said first linear axis, and said arm having a third length integrally extending from said second length in a direction away from said sleeve along a third linear axis which extends spaced and parallel to said first linear axis, said third length terminating at said arm second end, said rigid arm including a jacket of insulating material disposed thereon;
   d. a working tip electrode of predetermined configuration integrally formed at said arm second end; and
   e. a fourth length linearly extending at an obtuse angle ($A_3$) from said third length in a direction towards and intersecting said first, linear axis, said working tip electrode being integrally formed at the end of said fourth length opposite said third length and positioned on the side of said first linear axis opposite said third linear axis along which said third length lies, said electric conducting means, arm and working tip electrode forming a contiguous, electrically conductive path through which said electric current may travel and discharge at said working tip electrode.

2. The invention according to claim 1 wherein said working tip electrode is in the shape of a circular, planar spatula having a radial axis (r—r) perpendicular to a planar surface thereof.

3. The invention according to claim 2 wherein said planar spatula is oriented with said radial axis (r—r) intersecting said first linear axis at an obtuse angle ($A_6$).

4. An electro-surgical dissecting and cauterizing instrument for connection to a source of manually controllable, electric current, said instrument comprising:
   a. electric conducting means having proximal and distal ends, said electric conducting means proximal end forming a plug removably connecting said instrument to said source of manually controllable electric current;
   b. a rigid insulating sleeve having first and second ends and a constant outer diameter and lying along a first linear axis, said sleeve concentrically surrounding and electrically insulating said electric conducting means with said electric conducting means plug extending exteriorly of said sleeve first end and said electric conducting means distal end lying adjacent said sleeve second end, said conducting means providing a path through which said electric current may travel;
   c. a rigid, electrically conductive arm having first and second ends and an outer diameter smaller than said sleeve outer diameter, said arm first end electrically connected to said conducting means distal end and co-axially extending therefrom along said first linear axis for a first length thereof, said arm having a second length integrally extending from said first length and lying along a second linear axis which extends at an obtuse angle ($a_1$) to said first linear axis, and said arm having a third length integrally extending from said second length in a direction away from said sleeve along a third linear axis which extends spaced and parallel to said first linear axis, said third length terminating at said arm second end, said rigid arm including a jacket of insulating material disposed thereon; and d. a working tip electrode in the shape of an arcuate hook having a terminal end with the end of said hook opposite said terminal end integrally extending from said arm second end toward and intersecting said first linear axis with said hook terminal end being positioned on the side of said first linear axis opposite said third linear axis along which said arm third length lies, said electric conducting means, arm and working tip electrode forming a contiguous, electrically conductive path through which said electric current may travel and discharge at said working tip electrode.

5. An electro-surgical dissecting and cauterizing instrument for connection to a source of manually controllable, electric current, said instrument comprising:

a) electric conducting means having proximal and distal ends, said electric conducting means proximal end forming a plug for removably connecting said instrument to said source of manually controllable electric current;

b) a rigid insulating sleeve having first and second ends and a constant outer diameter and lying along a first linear axis, said sleeve concentrically surrounding and electrically insulating said electric conducting means with said electric conducting means plug extending exteriorly of said sleeve first end and said electric conducting means distal end lying adjacent said sleeve second end, said conducting means providing a path through which said electric current may travel;

c) a rigid, electrically conductive arm having first and second ends and an outer diameter substantially smaller than said sleeve outer diameter, said arm first end electrically connected to said conducting means distal end and linearly extending therefrom and lying along a second linear axis which extends at an acute angle ($A_4$) to said first linear axis; and d) a working tip electrode in the shape of a circular, planar spatula having a radial axis (R—R) perpendicular to a planar surface thereof and integrally formed at said arm second end and extending in a direction toward said first linear axis, said electric conducting means, arm and working tip electrode forming a contiguous, electrically conductive path through which said electric current may travel and discharge at said working tip electrode, said planar spatula being oriented with said radial axis (R—R) intersecting said first linear axis at an obtuse angle ($A_5$).

* * * * *